United States Patent [19]

Esser et al.

[11] Patent Number: 4,492,758
[45] Date of Patent: Jan. 8, 1985

[54] HYBRID VECTOR AND PROCESS FOR IMPROVING THE AMPLIFICATION AND EXPRESSION OF HYBRID VECTORS BY THE USE OF MITOCHONDRIAL DNA

[75] Inventors: Karl Esser; Ulf Stahl, both of Bochum; Paul Tudzynski, Gladbeck; Ulrich Kück, Bochum, all of Fed. Rep. of Germany

[73] Assignee: Hoechst Aktiengesellschaft, Frankfurt, Fed. Rep. of Germany

[21] Appl. No.: 383,205

[22] Filed: May 28, 1982

[30] Foreign Application Priority Data

Jun. 2, 1981 [DE] Fed. Rep. of Germany ....... 3121815

[51] Int. Cl.$^3$ .......................... C12N 1/00; C12N 1/20; C12N 5/00; C12N 5/02; C12N 1/14; C12P 21/00; C12P 19/34; C12P 15/00
[52] U.S. Cl. .................................... 435/317; 435/68; 435/91; 435/172.3; 435/253; 435/240; 435/241; 435/254
[58] Field of Search ..................... 435/68, 70, 91, 172, 435/253, 317, 172.3, 254

[56] References Cited

PUBLICATIONS

Stahl et al: Molec. Gen. Genet. 178, 639, (1980).
Zakian: Proc. Natl. Acad. Sci. USA 78, 3128, (1981).
Sugino: Biochem. Biophys. Res. Comm. 91, 1321, (1979).
Struhl et al: Proc. Natl. Acad. Sci. USA 76, 1035, (1979).
Cell, vol. 6, 231–244, Oct. 1975, entitled "Studies of a Mouse Mitochondrial DNA in Escherichia coli: Structure and Function of the Eucaryotic-Procaryotic Chimeric Plasmids".
Stahl et al., "Replication and Expression etc.", Proc. Natl. Acad. Sci. USA 79, 3641–3645, (1982).
Esser et al., Chem. Abstr. 93, 3776p, (1980).
Drouin, Chem. Abstr. 93, 164165d, (1980).
Pritchard et al., Chem. Abstr. 94, 27225e, (1981).
Kueck et al., Chem. Abstr. 95, 93504s, (1981).
Bartnik et al., Chem. Abstr. 95, 111591z, (1981).

Primary Examiner—Lionel M. Shapiro
Assistant Examiner—James Martinell
Attorney, Agent, or Firm—Curtis, Morris & Safford

[57] ABSTRACT

What are disclosed are a hybrid vector synthesized from a segment of mitochondrial DNA containing an origin of replication and, optionally, from a segment of a prokaryotic plasmid, and a method for improving the amplification and expression of hybrid vectors in eukaryotic host cells using mitochondrial DNA.

3 Claims, No Drawings

HYBRID VECTOR AND PROCESS FOR IMPROVING THE AMPLIFICATION AND EXPRESSION OF HYBRID VECTORS BY THE USE OF MITOCHONDRIAL DNA

It has been known since the first observations by Avery et al. (J.exp.Med. 79, 137–158 (1944)) that genetic information can be transferred from one bacterium to another. This laid the foundation for techniques developed in recent years, by which genetic information can be specifically transferred from one organism to another. These procedures, also referred to as "genetic manipulations", are described in detail in, for example, the text book "Genmanipulation and Gentherapie" ("Gene Manipulation and Gene Therapy") by Klingmüller, Springer-Verlag, 1976.

The decisive step in all genetic engineering work comprises introducing DNA into a new host organism with the aid of a vector. Hitherto, bacterial plasmids or double-stranded DNA from bacteriophages, i.e. prokaryotic DNA, have generally been used as such vectors. The discovery of restriction enzymes by Arber and Linn (Ann. Rev.Biochem. 38, 467–500 (1969)) was an essential prerequisite for the use of such vectors. These restriction enzymes are endonucleases which cleave the said vectors at specific sites without otherwise destroying their molecular structure. After mixing with DNA which has been similarly treated with endonucleases and has been taken from another organism, and after the addition of enzymes which bind the cleaved vector to the DNA fragments, namely of ligases, a new vector which in part contains other DNA fragments, namely a so-called hybrid vector, is formed. Hybrid vectors of this type can then be transferred to a host organism and multiply (amplify) therein, and this is because the prokaryotic vector DNA possesses an origin of replication. In favorable cases, this multiplication in the host organism (cloning) is also associated with expression of the genes present in the alien DNA introduced.

Hitherto, bacteria, namely various strains of *Escherichia coli* and of *Bacillus subtilis*, have been used virtually exclusively as host organisms for the uptake of hybrid vectors, their amplification and the expression of the alien DNA. Thus, it is known, for example, that the genetic information which is necessary for the formation of proinsulin and originates from animal cells can be transferred to *E. coli* with the aid of a vector and be expressed therefrom (Esser and Stahl: "Hybridization", in "Handbook of Biotechnology", Volume I, (1981)). However, this method has given rise to the following difficulties, which are also of practical significance:

(a) It has been shown that DNA from prokaryotes and DNA from eukaryotes have different structures in respect of their information content. Whereas, for prokaryotes, the whole of the DNA is transcribed into messenger RNA (transcription) in the course of genetic expression, this is not the case for eukaryotes. Double-stranded DNA does not have the genetic information stored in a continuous manner, but consists of information-containing segments (exons) and information-free segments (introns). In the transfer of these exons and introns to a prokaryote, its protein synthesis can therefore be disturbed.

(b) In contrast to eukaryotes, bacteria possess not the 80 S ribosomes, which play a part in protein synthesis in higher organisms, but only the 70 S ribosomes, which correspond to the mitochondrial ribosomes of higher organisms. Indeed, this could explain the fact that, although alien DNA often amplifies in prokaryotes, only a small expression of the gene products is determined.

(c) Moreover, it has been observed that, despite amplification and expression, the gene products of eukaryote DNA were occasionally destroyed in prokaryotes in a secondary process.

(d) Furthermore, it must be taken into account that, for example in the case of Bacillus subtilis, an instability of the transformation has appeared in some cases after successful transfer of eukaryote DNA, and this instability led to the fact that the genetic information transferred was already lost after a few generations in the bacterial population.

These difficulties are comprehensively illustrated by Macleod ("Nature", 285, 136 (1980)).

The object was therefore to overcome these disadvantages in order to permit a broader application of the gene manipulation of eukaryotic systems. This requires vectors which amplify well in eukaryotic cells and are also expressed. The systems developed hitherto for overcoming difficulties of this type have not been able to fulfil the hopes placed in them.

Thus, for example in the case of *Saccaromyces cerevisiae* (baker's yeast), there is a eukaryotic plasmid, namely so-called 2µ-DNA, which can be used as a vector for yeast itself (Hollenberg, "Progress in Botany", 42, 171–185 (1980)). However, after the transfer of genetic material from animal cells which codes for β-globin, this system could not differentiate exactly between introns and exons during transcription, i.e. the animal DNA was not exactly "spliced" (Beggs et al. "Nature", 283, 835–840 (1980)). Moreover, hybrid vectors of this type could only be multiplied poorly, even in yeast cells.

Even an attempt to use animal cells as host organisms, and therein to use viruses as vectors, has hitherto proved unsuccessful, if only because of the great effort associated therewith.

It has now been found that the abovementioned difficulties can be overcome by means of a hybrid vector which is synthesized from a segment of a mitochondrial DNA, containing an origin or replication, and optionally from a segment formed of a bacterial plasmid.

As double-stranded eukaryotic DNA, mitochondrial DNA is very suitable for taking over the function of a vector because it is not integrated into the chromosome system and is present in all cells in a relatively large number of copies. Moreover, as circular DNA, it is easy to separate from other DNA and, in particular, it is capable of amplifying on its own, since it contains an origin of replication.

In its structure, mitochondrial DNA is situated between chromosomal DNA and prokaryotic DNA. In fact, it contains both genes with introns and also genes without introns (Michaelis et al., "Progress in Botany", 42, 227–233 (1980)). Mitochondrial DNA is therefore suitable for use as a vector, both for a eukaryotic system and also for a prokaryotic system.

Mitochondrial DNA has a length of 5 to about 30 µm, depending on the organism. It is therefore frequently impossible, for technical reasons, to use the entire ring molecule as a vector. Consequently, it is necessary to cleave segments from the mitochondrial DNA which contain an origin of replication. Provided the mitochondrial DNA has already been mapped with the aid of restriction enzymes, and hence the position of the origin of replication is also known, it is possible, with the aid of endonucleases, directly to cleave those segments of the mitochondrial DNA which are capable of amplifying under suitable conditions. However, if the origin of replication has not yet been located, then a suitable segment of the mitochondrial DNA, carrying an origin of replication, must first be found.

A hybrid vector of this type is now obtainable, in a particularly simple manner, by using the pl-DNA found in the hypha fungus Podospora and already described previously in detail, as mitochondrial DNA for the preparation of a mitochondrial vector. This pl-DNA is a cyclic, covalently bonded DNA which is encountered as a rule in ageing mycelia of this fungus and shows a surprisingly larger number of similarities to the bacterial plasmids customarily used for genetic engineering work. In particular, reference is made in this context to the molecular weight of 2.4 kb, the contour length of 0.75 μm and the buoyant density of 1.699 g/cm$^3$ of the pl-DNA. In young *Podospora mycelia*, the pl-DNA is an integral component of the mitochondrial DNA. When it is released, the Podospora cells die. Free pl-DNA has its own origin of replication, can thus multiply on its own and is therefore also capable, after transfer to other cells via hypha fusion or protoplast fusion, of initiating ageing phenomena therein.

A hybrid vector can be synthesized, by methods which are in themselves known, from a pl-DNA molecule of this type and a bacterial plasmid such as pBR 322. This hybrid vector can be cloned both in *Escherichia coli* and also in Podospora. Expression of the gene products corresponding to both segments of the hybrid vector can be determined both in the bacterium and also in the fungus. After introduction of the hybrid vector, expression of the gene for ampicillin resistance can be detected, both in *Escherichia coli* and also in Podospora, as a result of the formation of a β-lactamase by the resistance gene for ampicillin present on the bacterial segment of the hybrid vector. Furthermore, the appearance of ageing phenomena, which can be attributed to the pl-DNA segment of the hybrid vector, is observed in the fungus.

It is obvious that the expression of ageing phenomena considerably hinders genetic engineering work with Podospora species. It has therefore proved advantageous, for the synthesis of hybrid vectors, to use Podospora strains which no longer show expression of senescence. Mutants of this type are known in the case of Podospora.

A process is thus made available for improving the amplification and expression of hybrid vectors which contain segments of prokaryotic DNA and eukaryotic DNA, wherein mitochondrial DNA is incorporated into the hybrid vector as eukaryotic DNA and this hybrid vector is used, in a manner which is in itself known, for the transformation of a prokaryotic or eukaryotic host cell. A vector of this type can be used both for the transfer of prokaryotic DNA and also for the transfer of eukaryotic DNA to a suitable host cell. This shows a route making it possible to overcome obstacles which have hitherto hindered the practical application of genetic engineering methods.

1. ISOLATION OF PL-DNA FROM PODOSPORA ANSERINA

The starting strain for the isolation of pl-DNA was the wild strain $s_1$ of *Podospora anserina*, as described by Esser in "Handbook of Genetics", Volume I, pages 531–551 (1974). Presenescent mycelium of this strain was grown for about 3 weeks, in a Fernbach flask, at 26° C., on a complete medium such as that described by Esser in the abovementioned publication. From this, the pl-DNA was isolated and purified by the procedure indicated by Stahl et al. in Molec.gen.Genet. 178, 639–646 (1980).

The pl-DNA isolated by this process (buoyant density in CsCl: 1.699 g/cm$^3$) was very heterogeneous with respect to the molecular weight. In fact, it consisted of a number of oligomeric cyclic molecules which nevertheless all had the same fundamental unit with a contour length of 0.75 μm. It was possible to observe that up to 13 fundamental units with the said contour length could come together to form a single molecule.

By digestion with particular restriction endonucleases having only a single cleavage site per fundamental unit, such as Sal I (=restriction enzyme from *Streptomyces albus*), Kpn I (=restriction enzyme from *Klebsiella pneumoniae*) and Bgl II (=restriction enzyme from *Bacillus globigii*), the whole of the DNA of molecules of this type could be converted to DNA segments of the uniform fundamental size with a contour length of 0.75 μm.

2. PREPARATION OF A HYBRID VECTOR

The preparation of a vector suitable for cloning in *E. coli* and Podospora, by binding the *E. coli* vector pBR 322 to the isolated pl-DNA, has already been described by Stahl et al. in "Molec.gen.Genet", 178, 639–646 (1980).

The preparation of a hybrid vector of this type from the *E. coli* vector pBR 322 and a restriction fragment (Sal 4) of mitochondrial DNA, which carries an origin of replication and is in part homologous to the pl-DNA, has not been disclosed hitherto. The following procedure is suitable for this purpose:

It is known that pl-DNA can be used to construct a vector because it carries an origin of replication. Accordingly, the synthesis of a hybrid vector from the intact (juvenile) mitochondrial DNA of Podospora can only be carried out successfully if the fragment removed from this DNA also contains an origin of replication. Such a fragment of juvenile mitochondrial DNA can be obtained by treatment with the restriction enzyme Sal I.

Thus, the plasmid pBR 322 and purified juvenile mitochondrial DNA of *Podospora anserina* were cleaved with the restriction enzyme Sal I and the resulting fragments were ligated in the same manner as that described by Stahl in the abovementioned literature reference. *E. coli* transformants having ampicillin resistance were selected from the hybrid vector thus formed. Their DNA was isolated and characterized by means of restriction analysis. Those hybrid plasmids which had actually taken up the DNA fragment to be transferred, namely the Sal 4 fragment in the present case, were selected in this way.

Hybrid vectors which contained this fragment showed an equally good transformation rate and replication in Podospora as the hybrid vectors from pBR 322 and pl-DNA, already prepared previously.

The present process for the preparation of a hybrid vector is generally applicable to any mitochondrial DNA, provided that its origin of replication is known.

3. TRANSFORMATION WITH HYBRID VECTORS IN PODOSPORA (a) Recipient strains

The process described below can in principle be carried out with a wild strain of *Podospora anserina*; in that case, expression of the hybrid plasmid introduced can be detected by the initiation of senescence symptoms. However, this is unsuitable for practical application because correspondingly transformed strains rapidly die irreversibly.

This problem can be solved by using long-lived mutant strains of Podospora. The following two strains have been used hitherto for this purpose:

The Podospora double mutant gr viv (grisea/vivax), which is described morphologically by Tudzynski and Esser in Molec.gen.Genet. 173, 71–84 (1979) and deposited as DSM 2099, shows no spontaneous ageing phenomena and contains no free pl-DNA. However, it can be transformed with pl-DNA and hybrid vectors and then shows senescence symptoms (Tudzynski et al. in Current Genet. 2, 181–184 (1980)). These symptoms are not so pronounced here, however, as for the wild strain, and in some cases are reversible by cold treatment.

The Podospora double mutant i viv (incoloris vivax), which is morphologically described by Esser and Keller in Molec.gen.Genet. 144, 107–110 (1976) and deposited as DSM 2098, shows no spontaneous and no induced senescence. However, because pl-DNA can replicate in it, it is outstandingly suitable as a recipient strain. Of course, the initiation of senescence cannot be used here as a selection feature for transformants.

(b) Transformation

The recipient strain was grown for 4 to 5 days, in a Fernbach flask, at 26° C., on a complete medium. The harvested mycelium was taken up in a protoplast buffer solution and the resulting mixture was then homogenized for about 20 seconds and finally incubated for 3 hours with a lytic enzyme mixture from *Trichoderma harzianum*, for the preparation of protoplasts.

The protoplasts were then washed twice with the protoplast buffer solution (0.5 mole of sucrose dissolved in a 0.1 molar solution of Tris-maleate, which was adjusted to a pH of 7 with NaOH). The protoplasts were then resuspended in this buffer solution, to which 10 millimoles of calcium chloride were also added, up to a final concentration of $5 \times 10^6$ to $5 \times 10^7$. The hybrid DNA, dissolved in TES buffer (0.05M Tris, 0.005 mole of EDTA, 0.05 mole of sodium chloride, pH 8) was added to this suspension up to a concentration of 5–10 μg/ml (wild strain) or 40 μg/ml (double mutant gr viv). In the comparison experiments, the TES buffer was used without any hybrid DNA. The mixture was left to stand at 26° C. for 15 minutes. The suspension was then diluted in a ratio of 1:10 with PEG buffer (20% strength polyethylene glycol 4,000, 10 millimoles of calcium chloride, 10 millimoles of Tris-HCl, pH 7.5) and incubated at 26° C. for 1 hour. The protoplasts were then transferred onto a regeneration medium.

The presence of a gene for a β-lactamase on the prokaryotic segment of the hybrid vector could be detected by the following test method:

Sorbose (15 g/l) was added to the regeneration medium for protoplasts, whereby the resulting colonies remained small and isolated. A β-lactamase detection reagent was then sprayed onto the medium or applied in a thin layer of soft agar, examples of such detection reagents being Padac (Schindler and Huber in "Enzyme Inhibitors", 169–176 (1980)) or Nitrocefin (O'Callaghan et al. in "Antimier. Agent Chemoth." 1, 283–288 (1972)). These reagents show a specific color change in the presence of β-lactamases; for example, Nitrocefin changes from yellow to red. In this way, transformed colonies could be identified, since Podospora (like all eukaryotes) does not synthesize any of its own β-lactamase. An increased sensitivity of the detection method was achieved by covering the colonies for a few hours with a filter which was impregnated with the above-mentioned lytic enzyme mixture. The β-lactamase test could then be carried out directly on the filter.

The selection of transformants could also be carried out by means of eukaryotic gene features additionally incorporated into the vector, for example by complementation of an auxotroph mutation in the recipient strain by means of a corresponding wild gene on the vector.

The transformants identified in this way were isolated and grown. They had to contain the hybrid plasmid because its amplification and expression was implied by the β-lactamase test. From such transformants, DNA was isolated which corresponded, in density and restriction pattern, to the hybrid plasmid used and which, on retransformation in *E. coli*, led to the formation of ampicillin-resistant colonies. Plasmid DNA obtained from these colonies contained sequences which were homologous to the Podospora DNA originally used.

The hybrid plasmids described were thus suitable for amplification and expression both in Podospora and also in *E. coli*.

4. PREPARATION OF A HYBRID VECTOR WITH AN ORIGIN OF REPLICATION OF THE MT-DNA OF ACREMONIUM CHRYSOGENUM

To obtain a restriction fragment containing an origin of replication from any eukaryote, it is possible, in addition to the direct transformation test in the final recipient organism (as described for Podospora), also to carry out a preselection in the baker's yeast *Saccharomyces cerevisiae*.

This eukaryotic microorganism is very easy to handle experimentally; in particular, it is possible to fall back on a well-established transformation system. This yeast transformation system has already been described in detail by Hinnen et al. (Proc. Nat. Acad. Sci. U.S. 75, 1,929–1,933, 1978). It includes the leucine-auxotrophic recipient strain AH-22 and vectors with the yeast 2-leucine gene from the wild strain of *S. cerevisiae*.

In the application according to the invention, starting vectors containing no eukaryotic origin of replication are used. These can only multiply in yeast if a restriction fragment containing such an origin of replication is integrated therein. In the case of the hypha fungus *Acremonium chrysogenum*, this process was used to isolate an origin of replication of the mt-DNA, the procedure being as follows:

The mitochondrial DNA of *Acremonium chrysogenum* Gams (synonym for *Cephalosporium acremonium* Corda) (Gams: Cephalosporium-type Molds, Fischer, Stuttgart 1971) has a size of 26.7 kb and is split by the restriction enzyme PstI into three fragments with sizes of 24.5, 1.85 and 0.53 kb. The fragments obtained were ligated, as described above, with the vector pDAM1, also cleaved by PstI (Beach et al.: Nature 284, 185–187, 1980). This vector consists of the bacterial plasmid pBR325 (Bolivar: Gene ("Genes") 4, 121–136, 1978) and the yeast 2-leucine gene (see above). It cannot multiply in yeast because it contains no eukaryotic origin of replication. Transformation experiments on the yeast strain AH-22 with hybrid vectors from pDAM1 and fragments of the mt-DNA are only successful if the integrated fragment contains a eukaryotic origin of replication. In the present case, it could be shown that this applies to the PstI/2 fragment in the case of *A. chrysogenum*. In fact, hybrid vectors with this fragment transform *S. cerevisiae* with high efficiency (>200 transformants per μg of DNA). Free plasmid DNA which is identical to the DNA used can be isolated from the transformants. Accordingly, the PstI/2 fragment clearly contains a eukaryotic origin of replication.

In principle, this process can be carried out withs any mitochondrial DNA.

We claim:

1. A hybrid vector synthesized from a fragment of mitochondrial DNA, containing a mitochondrial DNA origin of replication, of Acremonium or Podospora species.

2. A hybrid vector as claimed in claim 1, containing a segment of a prokaryotic plasmid.

3. A hybrid vector as claimed in claim 2, wherein the segment of the prokaryotic plasmid is a segment of a bacterial plasmid.

* * * * *